United States Patent
Lee et al.

(10) Patent No.: US 10,335,058 B2
(45) Date of Patent: Jul. 2, 2019

(54) APPARATUS FOR PERFORMING TIMED UP-AND-GO TEST

(71) Applicant: The Board of Regents of the Nevada System of Higher Education on Behalf of the University of Nevada, Las Vegas, Las Vegas, NV (US)

(72) Inventors: Szu-Ping Lee, Las Vegas, NV (US); Robbin Hickman, Henderson, NV (US); Janet Dufek, Henderson, NV (US)

(73) Assignee: The Board of Regents of the Nevada System of Higher Education on Behalf of the University of Nevada, Las Vegas, Las Vegas, NV (US)

( * ) Notice: Subject to any disclaimer, the term of this patent is extended or adjusted under 35 U.S.C. 154(b) by 351 days.

(21) Appl. No.: 15/033,850

(22) PCT Filed: Nov. 14, 2014

(86) PCT No.: PCT/US2014/065780
§ 371 (c)(1),
(2) Date: May 2, 2016

(87) PCT Pub. No.: WO2015/073875
PCT Pub. Date: May 21, 2015

(65) Prior Publication Data
US 2016/0249830 A1    Sep. 1, 2016

Related U.S. Application Data

(60) Provisional application No. 61/904,693, filed on Nov. 15, 2013.

(51) Int. Cl.
*A61B 5/00* (2006.01)
*A61B 5/11* (2006.01)

(52) U.S. Cl.
CPC .............. *A61B 5/11* (2013.01); *A61B 5/0022* (2013.01); *A61B 5/1116* (2013.01);
(Continued)

(58) Field of Classification Search
CPC ....... A61B 5/11; A61B 5/1116; A61B 5/1117; A61B 5/6891; A61B 5/0022; A61B 2562/0247
See application file for complete search history.

(56) References Cited

U.S. PATENT DOCUMENTS 5,536,068 A * 7/1996 Valentor ................. A47C 3/38
                                                    297/183.1
5,570,301 A * 10/1996 Barrus ................... A61B 5/103
                                                    702/150

(Continued)

FOREIGN PATENT DOCUMENTS

EP           2878261 A1 *  11/2013  ........... A61B 5/0002

OTHER PUBLICATIONS

Bischoff, et al., "Identifying a cut-off point for normal mobility: a comparison of the timed 'up and go' test in community-dwelling and institutionalized elderly women." Age and Ageing. 2003; 32(3): 315-20.

(Continued)

*Primary Examiner* — Sean P Dougherty
(74) *Attorney, Agent, or Firm* — Ballard Spahr LLP

(57) ABSTRACT

A chair enabling standardized performance testing under Timed Up and Go procedures. The chair has a seat portion, a base portion, a support element, a force sensor, a timer, and a processor. The processor initiates timing of the standardized performance test in response to receiving an output signal corresponding to a force value less than or equal to a minimum threshold force. The processor ceases timing of the standardized performance test in response to receiving (Continued)

an output signal corresponding to a force greater than or equal to a maximum threshold force. The processor determines a time interval of the standardized performance test based upon the output of the timer.

20 Claims, 3 Drawing Sheets

(52) U.S. Cl.
CPC .......... *A61B 5/1117* (2013.01); *A61B 5/6891* (2013.01); *A61B 2562/0247* (2013.01)

(56) References Cited

U.S. PATENT DOCUMENTS

| | | | |
|---|---|---|---|
| 2003/0100264 A1* | 5/2003 | Schroeder | G06F 1/1601 455/66.1 |
| 2006/0293613 A1* | 12/2006 | Fatehi | A61B 5/1036 600/587 |
| 2007/0208279 A1* | 9/2007 | Panella | A61B 5/1124 600/595 |
| 2008/0007103 A1* | 1/2008 | Welles | A61B 5/11 297/330 |
| 2008/0194923 A1* | 8/2008 | Smith | A61B 5/1116 600/300 |
| 2008/0242521 A1* | 10/2008 | Einav | A61B 5/1116 482/110 |
| 2009/0058661 A1* | 3/2009 | Gleckler | A61B 5/103 340/573.7 |
| 2012/0116251 A1* | 5/2012 | Ben-Shalom | A61B 5/11 600/587 |
| 2012/0330113 A1* | 12/2012 | Kogure | A61B 5/0245 600/301 |
| 2013/0012786 A1* | 1/2013 | Horseman | G06F 19/3418 600/301 |
| 2013/0281887 A1* | 10/2013 | David | A61B 5/0205 600/587 |
| 2014/0330186 A1* | 11/2014 | Hyde | A61F 5/02 602/19 |
| 2014/0364784 A1* | 12/2014 | Hyde | A61F 5/028 602/19 |
| 2015/0015399 A1* | 1/2015 | Gleckler | A61B 5/1116 340/573.7 |

OTHER PUBLICATIONS

International Search Report and Written Opinion dated Feb. 11, 2015, for application PCT/US2014/065780, filed on Nov. 14, 2014 and published as WO 2015/073875 on May 21, 2015 (Applicant—The Board of Regents of the Nevada System of Higher Learning on Behalf of the University of Nevada, Las Vegas // Inventor—Lee, et al.;) (20 pages).

International Preliminary Report on Patentability dated May 17, 2016, for application PCT/US2014/065780, filed on Nov. 14, 2014 and published as WO 2015/073875 on May 21, 2015 (Applicant—The Board of Regents of the Nevada System of Higher Learning on Behalf of the University of Nevada, Las Vegas // Inventor—Lee, et al.;) (12 pages).

* cited by examiner

APPARATUS FOR PERFORMING TIMED UP-AND-GO TEST

CROSS-REFERENCE TO RELATED PATENT APPLICATION

This application claims the benefit of and priority under 35 U.S.C. § 371 of PCT/US2014/065780, filed Nov. 14, 2014, which claims the benefit under 35 U.S.C. § 119(e) of U.S. Provisional Patent Application No. 61/904,693, which was filed on Nov. 15, 2013, which are incorporated by reference herein in their entireties.

BACKGROUND

In the evaluation of patient status and progress, numerous physical performance tests have been developed and approximately standardized over the years. The objective of these tests is to provide comparable measurements which can be correlated with the observable effects of conditions on patients. Specifically, the goal of such tests is to quantitatively measure a person's mobility and physical performance. As physical performance is highly associated with quality of life and risk of falling, accurate monitoring of physical performance in older adults is necessary and important.

The Timed Up and Go (TUG) test is a simple test used to assess a person's mobility. To perform the test well, it requires both static and dynamic balance, strength, vision, and cognition. The test measures the time that a person takes to rise from a chair, walk three meters, turn around, walk back to the chair, and sit down. The TUG is used frequently in the elderly population, as it is easy to administer and can generally be completed by most older adults.

One source suggests that scores of 10 seconds or less from a TUG test indicate normal mobility, 11-20 seconds are within normal limits for frail elderly and disabled patients, and greater than 20 seconds means the person needs assistance outside and indicates further examination and intervention. A score of fourteen seconds or more suggests that the person may be prone to falls. Alternatively, a recommended practical cut-off value for the TUG to indicate normal versus below normal performance is 12 seconds. A study by Bischoff et al. showed the 10th to 90th percentiles for TUG performance were 6.0 to 11.2 seconds for community-dwelling women between 65 and 85 years of age, and determined that this population should be able to perform the TUG in 12 seconds or less. Bischoff et al. "Identifying a cut-off point for normal mobility: A comparison of the timed 'up and go' test in community-dwelling and institutionaliseds elderly women". *Age and Ageing* 32 (3): 315-20. TUG performance has been found to decrease significantly with mobility impairments. Residential status and physical mobility status have been determined to be significant predictors of TUG performance.

Research has shown the TUG test has excellent interrater (interclass correlation coefficient (ICC)=0.99) and intrarater reliability (ICC=0.99). The test score also correlates well with gait speed (r=−55), scores on the Berg Balance Scale (r=−0.72), and the Barthel Index (r=−0.51). Many studies have shown good test-retest reliability in specific populations such as community-dwelling older adults and people with Parkinson's disease.

The Timed Up-and-Go Test Procedure:

The height of a chair or bench is adjusted so that when the subject is seated on the chair or bench, his or her feet are flat on the floor with knees flexed at 90 degrees. Once positioned, the standardized procedure for the TUG test is followed. Subjects are observed and timed from the instant they rise from the chair or bench, walk a fixed distance (3, 6, or 9 meters), navigate around an obstacle on the floor (i.e. a cone), and return to a fully seated position in the chair or bench. Subjects wear their regular footwear and foot orthotic(s) during this test.

Subjects are instructed to be seated and ready for the test on the word "ready", and begin the test on the word "go". The goal of the test is to "stand up, walk at a fast pace, turn, and walk at a fast pace back to the bench and sit down." A test administrator records the time using a stop-watch. Another test administrator makes sure that the data are recorded and exported successfully. Typically, three trials are collected from each subject.

SUMMARY

The present technology includes a method of performing a standardized version of the Timed Up and Go test and equipment that is used in that test. As disclosed herein, a chair can be constructed to better enable standardized performance of TUG testing.

Described herein, in one aspect, is a chair for administering a standardized performance test (e.g., a TUG test) to a patient. The chair can have a seat portion, a base portion, a support element, a force sensor, a timer, and a processor. The support element can extend between the base portion and the seat portion and can be configured to support the seat portion. A position of the seat portion relative to the base portion can be selectively adjustable relative to a vertical axis. The force sensor can be operatively coupled to one of the seat portion, the base portion, and the support element. The force sensor can be configured to produce an output signal indicative of the force applied to the force sensor. The timer can be configured to provide an output indicative of a recorded time interval. The processor can be positioned in operative electrical communication with the force sensor and the timer. The processor can be configured to receive the output signal from the force sensor. The processor can be configured to initiate timing of the standardized performance test by the timer in response to receiving an output signal corresponding to a force value less than or equal to a minimum threshold force. The processor can be configured to cease timing of the standardized performance test by the timer in response to receiving an output signal corresponding to a force greater than or equal to a maximum threshold force. The processor can be further configured to determine a time interval of the standardized performance test based upon the output of the timer.

Methods of using the chair are also described. For example, in one aspect, a method of administering a standardized performance test to a patient is described. The method can include: seating the patient on the chair; using the processor of the chair to initiate timing of the standardized performance test by the timer in response to receiving an output signal corresponding to a force value less than or equal to the minimum threshold force; using the processor of the chair to cease timing of the standardized performance test by the timer in response to receiving an output signal corresponding to a force greater than or equal to the maximum threshold force; and using the processor to determine a time interval of the standardized performance test based upon the output of the timer. The receipt of the output signal corresponding to a force value less than or equal to the minimum threshold value can occur as the patient rises from the chair, and the receipt of the output signal corresponding to a force value greater than or equal to the maximum threshold value can occur as the patient is reseated in the chair.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

These and other features of the preferred embodiments of the invention will become more apparent in the detailed description in which reference is made to the appended drawings wherein.

DETAILED DESCRIPTION

Figure 1:
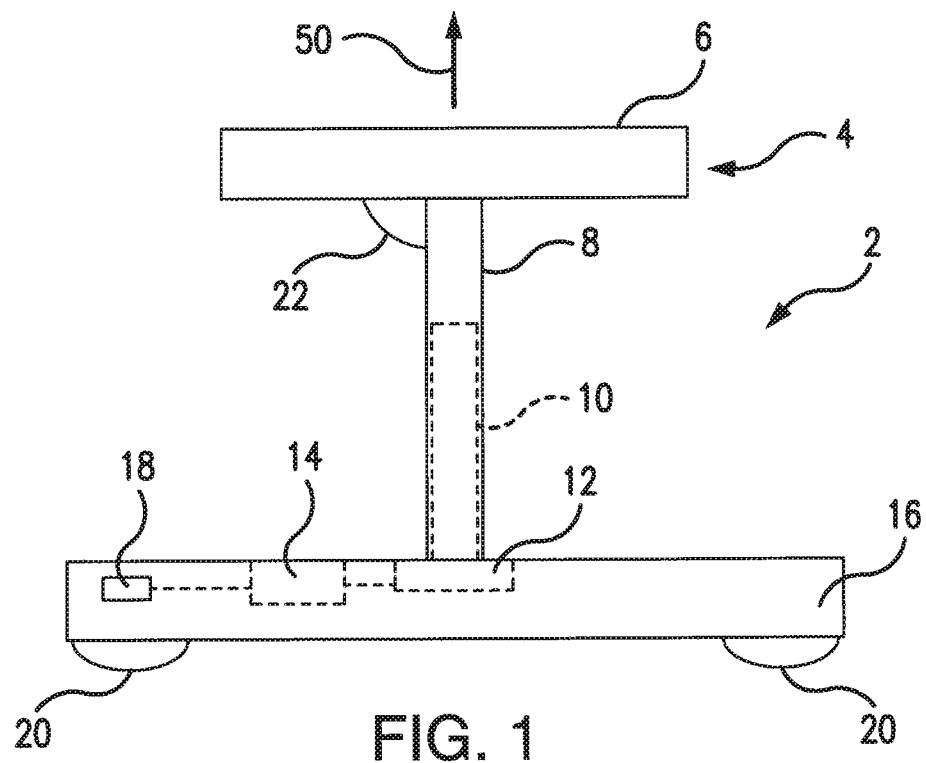
FIG. 1 shows a side view of an exemplary chair as disclosed herein.
Figure 2:
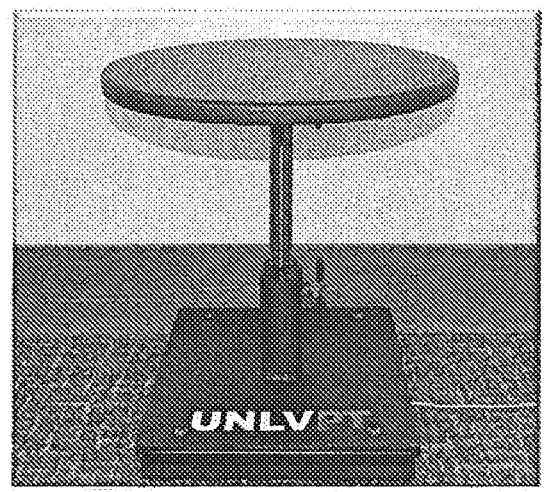
FIG. 2 is an image showing a front perspective view of an exemplary chair as disclosed herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a force sensor" can include two or more such force sensors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Disclosed herein, in various aspects, is a method of performing a standardized version of the Timed Up and Go (TUG) test, as well as a system for performing such a standardized performance test. The system for performing the standardized performance test can be provided as a chair that is constructed to better enable standardized performance TUG testing.

Figure 3:
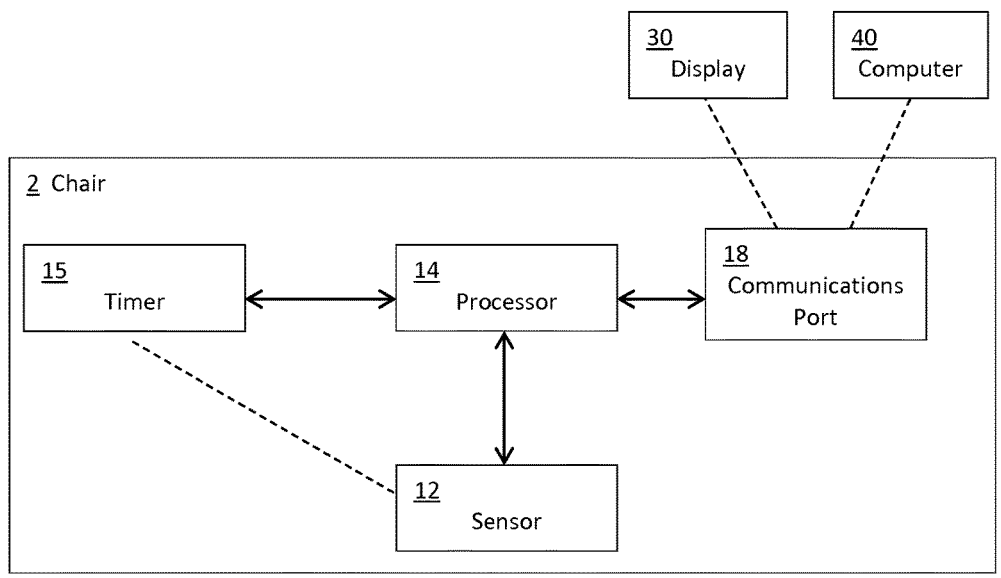
FIG. 3 is a schematic diagram showing an exemplary connection structure between elements of the chair and external elements, such as a display and a computer.
Figure 4A:
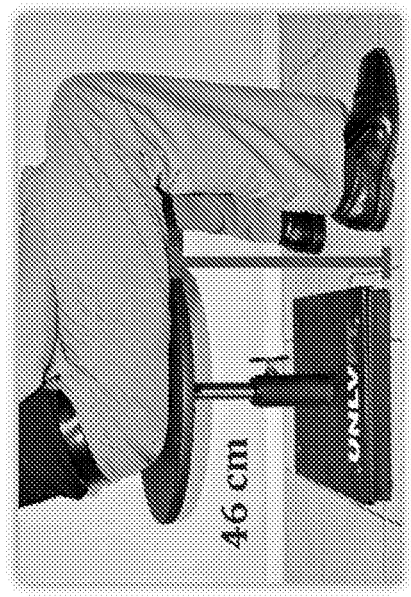
FIGS. 4A-4B are images depicting the selective adjustment of the height of the seat portion of an exemplary chair as disclosed herein.
Figure 4B:
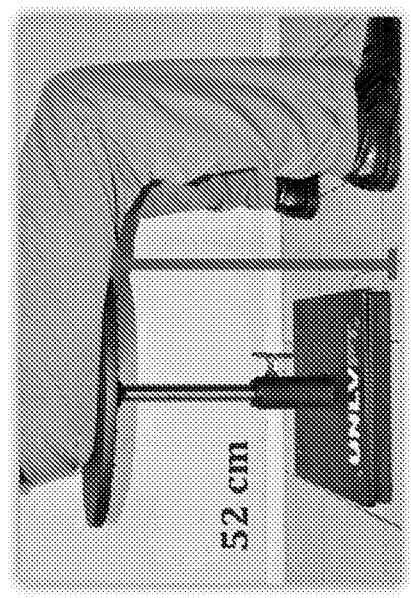

In exemplary aspects, and with reference to FIGS. 1-4B, disclosed is a chair for administering a standardized performance test to a patient. In these aspects, the chair can comprise a seat portion, a base portion, a support element, a force sensor, a timer, and a processor. The support element can extend between and be coupled or secured to the base portion and the seat portion such that the support element supports the seat portion. As shown in FIGS. 4A-4B, it is contemplated that a position of the seat portion relative to the base portion can be selectively adjustable relative to a vertical axis. In one aspect, the force sensor can be operatively coupled to one of the seat portion, the base portion, and the support element. In this aspect, the force sensor can be configured to produce an output signal indicative of the force applied to the force sensor. Optionally, the force sensor can be positioned within one of the seat portion, the base portion, and the support element. Alternatively, the force sensor can be secured to an external surface of one of the seat portion, the base portion, and the support element. In another aspect, the timer can be configured to provide an output indicative of a recorded time interval.

In an additional aspect, and with reference to FIGS. 1 and 3, the processor can be positioned in operative electrical communication with the force sensor and the timer. In this aspect, the processor can be configured to receive the output signals from the force sensor and the timer. In operation, the processor can be configured to initiate timing of the standardized performance test by the timer in response to receiving an output signal corresponding to a force value less than or equal to a minimum threshold force (indicating that the patient is no longer seated on the chair). The processor can be further configured to cease timing of the standardized performance test by the timer in response to receiving an output signal corresponding to a force greater than or equal to a maximum threshold force (indicating the patient has returned to a seated position on the chair). The processor can be still further configured to determine a time interval of the standardized performance test based upon the output of the timer.

It is contemplated that the force sensor of the chair can be any conventional sensor that is functionally capable of measuring the range of weights which patients or other test subjects may provide. For example, it is contemplated that the force sensor can have a range of sensitivity in a range of weights between about 10 and about 500 pounds, with a minimum range of sensitivity in a range of weights between about 30 and about 300 pounds. However, any sensitivity range can be used. Although pressure or force is being measured by the force sensor, it is understood that the force sensor is fundamentally providing a weighing operation. In various aspects, it is contemplated that the force sensor can be electrical, electromechanical, or mechanical with a reading function (optical or electronic) associated with the mechanical portion of the sensor.

In exemplary aspects, the support element can comprise means for adjusting the position of the seat portion relative to the base portion. Optionally, in these aspects, the means for adjusting the position of the seat portion can comprise a telescoping mechanism as is known in the art. In these aspects, the telescoping mechanism can be configured to effect selective extension and retraction of the support element relative to the vertical axis as shown in FIGS. 4A-4B. It is contemplated that movement of the support element relative to the vertical axis can effect a corresponding movement of the seat portion relative to the vertical axis. It is contemplated that the telescoping mechanism can be any conventional telescoping mechanism, such as, for example and without limitation, a threaded engagement system in which a first element of the telescoping mechanism is threadably received within a second element of the telescoping mechanism to adjust the combined operative length defined by the first and second elements of the telescoping system. In such a threaded engagement system, it is contemplated that the first element of the threaded engagement system can be secured to one of the base portion and the seat portion while the second element of the threaded engagement system can be secured to the other of the base portion and the seat portion. Optionally, in other exemplary aspects, the means for adjusting the position of the seat portion can comprise can comprise a slide engagement mechanism, a step movement mechanism, or any other mechanism for effecting axial movement as is known in the art. Although not necessarily desired, it is contemplated that the means for adjusting the position of the seat portion can comprise separate extending elements. In further exemplary aspects, it is contemplated that the height of the top surface of the seat portion relative to the base portion (measured relative to the vertical axis) can be selectively adjustable between about 10 and about 30 inches.

In exemplary aspects, and with reference to FIGS. 1 and 3, the processor can be configured to receive an output signal from the force sensor indicative of an initial force from the patient when the patient is seated on the seat portion. In these aspects, the processor can be configured to determine the minimum threshold force as a first selected portion of the initial force. The processor can be further configured to determine the maximum threshold force as a second selected portion of the initial force. In further exemplary aspects, the processor can be configured to receive an output signal from the force sensor when the patient is seated on the seat portion. In these aspects, the processor can be configured to determine a maximum force applied by the seated patient, and the processor can be configured to determine the minimum threshold force as a selected percentage of the determined maximum force applied by the seated patient.

In exemplary aspects, the initial force can correspond to a seated body weight of the patient. In one aspect, the first selected portion of the initial force can range from about 10% to about 30% of the initial force (about 70% to about 90% of the initial force being removed from the seat portion). In this aspect, the second selected portion of the initial force can optionally range from about 50% to about 95% of the initial force, and, more preferably, from about 70% to about 90% of the initial force. In another aspect, the first selected portion of the initial force can correspond to about 10% of the initial force (about 90% of the initial force being removed from the seat portion). In this aspect, the second selected portion of the initial force can optionally correspond to about 90% of the initial force. Thus, if a patient weighs 150 pounds, the timer can begin activity when the force sensor indicates that the weight (force) on the seat portion has been reduced by 50%, 60%, 70%, 80%, 90% or another predetermined percentage) or by a specific relative amount of weight (e.g., 100 pounds). Similarly, the processor can establish the maximum threshold force in relation to the initial force or the minimum threshold force (e.g., the same absolute force or weight or a percentage of the initial pressure or the minimum threshold force). Optionally, it is contemplated that the threshold force for detecting standing and sitting force can be a single force value.

Optionally, the chair can further comprise a display in operative communication with the processor. In exemplary aspects, the processor can be configured to transmit the time interval to the display. In some optional aspects, the display can be secured to a portion of the chair, such, as for example and without limitation, a portion of the base portion of the chair. Alternatively, it is contemplated that the display can be provided as a freestanding component that can be selectively secured to the chair or positioned a spaced distance from the chair. In one aspect, it is contemplated that the display can be positioned in operative communication with the processor through an external communications port, which can be any conventional communications port as is known in the art. In this aspect, the communications port can optionally be an information port as is known in the art. Alternatively, it is contemplated that the communications port can optionally be a wireless connection as is known in the art. In further exemplary aspects, it is contemplated that the external communications port can provide communication between the processor and an external computer as further disclosed herein. For example, in these aspects, the processor can be configured to transmit the determined time interval for a given test to a memory of the external computer for storage and/or further processing.

It is contemplated that the seat portion of the chair can be standardized and be relatively firm, if not rigid. In exemplary aspects, the seat portion can comprise a non-cushioned wood, metal, composite, or polymeric panel or block. It is further contemplated that some minimum cushioning can be provided for contact comfort. However, it is understood that excessive cushioning can adversely impact the performance characteristics of individuals and the accuracy of the force measurement.

In use, it is contemplated that the adjustment of the height of the chair as disclosed herein can be fundamentally used to compensate for height differences in patients. Even though the timing parameters are standardized, it is contemplated that the height of the chair can impact the timing interval between the time when a patient applies the minimum threshold pressure and the time when the patient applies the maximum threshold pressure. For example, it may be easier for shorter persons to rise from an elevated seat when compare to taller persons. As standardization of results desirably attempts to provide uniformity of test parameters without regard to height and other personal characteristics that are not relevant to physical mobility, it is contemplated that the design of the chair can have a significant impact on that standardization. In exemplary aspects, the seat portion can be flat or slightly receptor shaped (with indentations). In other exemplary aspects, the seat portion can be substantially horizontal. In still other exemplary aspects, the position and/or orientation of the seat portion can be selectively adjustable as further disclosed herein.

FIG. 1 shows a side view of an exemplary chair 2 as disclosed herein. The chair 2 is shown with a seat portion 4 having a top surface 6. A test subject (patient) would sit on the top surface 6, which can be generally flat. Pressure or weight can be transmitted from the seat portion 4 through the support element 8, which can optionally comprise a telescoping mechanism 10, which can permit adjustment of the position of the seat portion 4 relative to the vertical axis 50. Although not shown, it is contemplated that the telescoping mechanism 10 can optionally be headed, have step locks, and the like. The support element 8 can be operatively coupled to the pressure/weight sensor 12, which can be positioned within the support element or within or on the base portion 16. The timer 15 can optionally be incorporated as part of sensor 12. Alternatively, it is contemplated that the timer 15 can optionally be provided as part of the processor 14. It is further contemplated that the timer 15 can be provided as a freestanding element. The processor 14 can be any conventional processing element as is known in the art. In exemplary aspects, the processor 14 can be provided as part of a computing device, including, for example and without limitation, a computer as is known in the art. In other exemplary aspects, the processor 14 can be a lower logic processor such as a field programmable gated array or ASIC. It is contemplated that the chair 2 can be provided with an on/off switch as is known in the art to permit selective activation and inactivation of the electrical components of the chair.

In further exemplary aspects, the processor 14 can also be positioned in operative communication with a display 30 or a computer 40 through an external communication port 18, such as, for example and without limitation, a 110 port, a USB port, a wireless transmitter, and the like. Optionally, and as further disclosed herein, it is contemplated that the processor 14 can be configured to produce an output to be shown by the display 30. In other optional aspects, it is contemplated that a memory of the computer 40 can be configured to receive and store outputs of the processor 14. In further optional aspects, it is contemplated that the processor 14 can be positioned in operative communication with a processor of the computer 40 such that transmission of an output of the processor 14 to the processor of computer 40 is configured to initiate a corresponding action (e.g., further processing) by the computer 40. Optionally, it is contemplated that the display 30 can be physically connected or coupled to the chair 2. Alternatively, the display 30 can be positioned a spaced distance from the chair 2.

Alternative or optional subcomponents such as rollers 20 and an angle adjustment 22 for the seat portion 4 are also shown in FIG. 1. These subcomponents are conventional and are not described in detail herein.

A method of performing a timed up and go test can comprise steps consistent with the conventional TUG test, including, for example and without limitation, seating a test subject on the seat of the chair, initiating a time interval measurement by the timer by the processor recognizing attainment of the minimum threshold force, and ending the time interval measurement when the test subject has reseated on the seat of the chair and maximum threshold force has been attained.

Thus, in one aspect, a method of administering a standardized performance test to a patient can comprise seating the patient on the chair. In another aspect, the method of administering the standardized performance test can comprise using the processor of the chair to initiate timing of the standardized performance test by the timer in response to receiving an output signal corresponding to a force value less than or equal to the minimum threshold force. In this aspect, it is contemplated that receipt of the output signal corresponding to a force value less than or equal to the minimum threshold value can occur as the patient rises from the chair. In an additional aspect, the method of administering the standardized performance test can comprise using the processor of the chair to cease timing of the standardized performance test by the timer in response to receiving an output signal corresponding to a force greater than or equal to the maximum threshold force. In this aspect, the receipt of the output signal corresponding to a force value greater than or equal to the maximum threshold value can occur as the patient is reseated in the chair. In a further aspect, the method of administering the standardized performance test can comprise can comprise using the processor to determine a time interval of the standardized performance test based upon the output of the timer.

Optionally, in exemplary aspects, the method of administering the standardized performance test can comprise selectively adjusting a vertical position of the seat portion relative to the base portion.

Optionally, in other exemplary aspects, the method of administering the standardized performance test can comprise using the processor to transmit the time interval to a display and/or an external computing device. In these aspects, the processor can optionally transmit the time interval to the display and/or external computing device through an information port. Alternatively, the processor can optionally transmit the time interval to the display and/or external computing device through a wireless connection.

In the operation of the timing function for the stand-up portion of the procedure disclosed herein, it is contemplated that alternative provisions can be made to add further insight into individual test subject performance. Although the test is well defined and its results and interpretation are well understood, additional added value can be provided by the test. As coordination, balance, and specific strengths are being measured by the test, it is contemplated that variations within other time frames of the system can also be provided, especially during the stand-up and sit-down phase.

In operation, it is contemplated that different test subjects can initiate the test with one or more false starts, which can provide valuable insight into the test subject's overall ability. For example, if a test subject has two, three or more movements in the chair at the beginning of a test where the force goes from 100% to 70%, 50%, 40% and the like (with the triggering force threshold set at 90% of the weight being removed from the chair, or 10% of the seated weight), these false starts could be indicative of an inability to easily raise oneself from the chair, which would be useful additional information regarding the overall physical capabilities of the test subject. Note that pressure alterations in the 5%, 10% or even 30% range might be deemed insignificant events, such as merely the test subject shifting position on the seat. In exemplary aspects, and as further disclosed herein, it is contemplated that the processor of the chair can be configured to transmit the output signals of the force sensor to a memory for storage and analysis. It is further contemplated that the processor of the chair or an external processing element (for example, a processor of an external computer)

can be positioned in operative communication with the memory to permit analysis of the output signals of the force sensor. It is still further contemplated that such analysis of the output signals can permit detection of abnormalities or unexpected characteristics of the application of force by the test subject, such as, for example and without limitation, an incremental, gradual decrease in the application of force during standing as discussed above. It is still further contemplated that such analysis can permit detection of physical performance issues that are not clearly reflected in the results of the TUG test.

Other structural modifications and method alterations are within the skill of the ordinary artisan and may be practiced within the scope of the present technology.

Exemplary Aspects

In one exemplary aspect, disclosed herein is a chair for administering a standardized performance test to a patient, comprising: a seat portion; a base portion; a support element extending between the base portion and the seat portion, the support element configured to support the seat portion, wherein a position of the seat portion relative to the base portion is selectively adjustable relative to a vertical axis; a force sensor operatively coupled to one of the seat portion, the base portion, and the support element, wherein the force sensor is configured to produce an output signal indicative of the force applied to the force sensor; a timer configured to provide an output indicative of a recorded time interval; and a processor positioned in operative electrical communication with the force sensor and the timer, the processor being configured to receive the output signal from the force sensor, wherein the processor is configured to initiate timing of the standardized performance test by the timer in response to receiving an output signal corresponding to a force value less than or equal to a minimum threshold force, wherein the processor is configured to cease timing of the standardized performance test by the timer in response to receiving an output signal corresponding to a force greater than or equal to a maximum threshold force, and wherein the processor is configured to determine a time interval of the standardized performance test based upon the output of the timer.

In other exemplary aspects, the force sensor is positioned within the base portion.

In other exemplary aspects, the force sensor is positioned within the support element.

In other exemplary aspects, the support element comprises a telescoping mechanism configured to effect selective extension and retraction of the support element relative to the vertical axis, and movement of the support element relative to the vertical axis is configured to effect a corresponding movement of the seat portion relative to the vertical axis.

In other exemplary aspects, the telescoping mechanism comprises a threaded engagement system.

In other exemplary aspects, the processor is configured to receive an output signal from the force sensor indicative of an initial force from the patient when the patient is seated on the seat portion, and the processor is configured to determine the minimum threshold force as a first selected portion of the initial force.

In other exemplary aspects, the processor is further configured to determine the maximum threshold force as a second selected portion of the initial force.

In other exemplary aspects, the processor is configured to receive an output signal from the force sensor when the patient is seated on the seat portion, the processor is configured to determine a maximum force applied by the seated patient, and the processor is configured to determine the minimum threshold force as a selected percentage of the determined maximum force applied by the seated patient.

In other exemplary aspects, the chair further comprises a display in operative communication with the processor, and the processor is configured to transmit the time interval to the display.

In other exemplary aspects, the display is positioned in operative communication with the processor through an information port.

In other exemplary aspects, the display is positioned in operative communication with the processor through a wireless connection.

In other exemplary aspects, the initial force corresponds to a seated body weight of the patient, and the first selected portion of the initial force ranges from about 10% to about 30% of the initial force (about 70% to about 90% of the initial force being removed from the seat portion).

In other exemplary aspects, the second selected portion of the initial force ranges from about 70% to about 90% of the initial force.

In other exemplary aspects, the initial force corresponds to a seated body weight of the patient, and the first selected portion of the initial force corresponds to about 10% of the initial force (about 90% of the initial force being removed from the seat portion).

In other exemplary aspects, the second selected portion of the initial force corresponds to about 90% of the initial force.

In another exemplary aspect, disclosed is a method of administering a standardized performance test to a patient, comprising: seating the patient on the chair; using the processor of the chair to initiate timing of the standardized performance test by the timer in response to receiving an output signal corresponding to a force value less than or equal to the minimum threshold force, wherein the receipt of the output signal corresponding to a force value less than or equal to the minimum threshold value occurs as the patient rises from the chair; using the processor of the chair to cease timing of the standardized performance test by the timer in response to receiving an output signal corresponding to a force greater than or equal to the maximum threshold force, wherein the receipt of the output signal corresponding to a force value greater than or equal to the maximum threshold value occurs as the patient is reseated in the chair; and using the processor to determine a time interval of the standardized performance test based upon the output of the timer.

In other exemplary aspects, the method further comprises selectively adjusting a vertical position of the seat portion relative to the base portion.

In other exemplary aspects, the method further comprises using the processor to transmit the time interval to a display.

In other exemplary aspects, the processor transmits the time interval to the display through an information port.

In other exemplary aspects, the processor transmits the time interval to the display through a wireless connection.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed:

1. A chair for administering a standardized performance test to a patient, comprising:
   a seat portion;
   a base portion;
   a support element extending between the base portion and the seat portion, the support element configured to support the seat portion, wherein a position of the seat portion relative to the base portion is selectively adjustable relative to a vertical axis;
   a force sensor operatively coupled to one of the seat portion, the base portion, and the support element, wherein the force sensor is configured to produce an output signal indicative of the force applied to the force sensor;
   a timer configured to provide an output indicative of a recorded time interval; and
   a processor positioned in operative electrical communication with the force sensor and the timer, the processor being configured to receive the output signal from the force sensor,
   wherein the processor is configured to initiate timing of the standardized performance test by the timer in response to receiving an output signal from the force sensor corresponding to a force value less than or equal to a minimum threshold force, wherein the minimum threshold force is indicative of a rising of the patient from the seat portion of the chair, wherein the processor is configured to cease timing of the standardized performance test by the timer in response to receiving an output signal from the force sensor corresponding to a force greater than or equal to a maximum threshold force, wherein the maximum threshold force is indicative of a reseating of the patient on the seat portion of the chair, and wherein the processor is configured to determine a time interval of the standardized performance test based upon the output of the timer.

2. The chair of claim 1, wherein the force sensor is positioned within the base portion.

3. The chair of claim 1 wherein the support element comprises a telescoping mechanism configured to effect selective extension and retraction of the support element relative to the vertical axis, and wherein movement of the support element relative to the vertical axis is configured to effect a corresponding movement of the seat portion relative to the vertical axis.

4. The chair of claim 3, wherein the telescoping mechanism comprises a threaded engagement system.

5. The chair of claim 1, wherein the processor is configured to receive an output signal from the force sensor indicative of an initial force from the patient when the patient is seated on the seat portion, and wherein the processor is configured to determine the minimum threshold force as a first selected portion of the initial force.

6. The chair of claim 5, wherein the processor is further configured to determine the maximum threshold force as a second selected portion of the initial force.

7. The chair of claim 1, wherein the processor is configured to receive an output signal from the force sensor when the patient is seated on the seat portion, wherein the processor is configured to determine a maximum force applied by the seated patient, and wherein the processor is configured to determine the minimum threshold force as a selected percentage of the determined maximum force applied by the seated patient.

8. The chair of claim 1, further comprising a display in operative communication with the processor, wherein the processor is configured to transmit the time interval to the display.

9. The chair of claim 8, wherein the display is positioned in operative communication with the processor through an information port.

10. The chair of claim 8, wherein the display is positioned in operative communication with the processor through a wireless connection.

11. The chair of claim 6, wherein the initial force corresponds to a seated body weight of the patient, and wherein the first selected portion of the initial force ranges from about 10% to about 30% of the initial force (about 70% to about 90% of the initial force being removed from the seat portion).

12. The chair of claim 11, wherein the second selected portion of the initial force ranges from about 70% to about 90% of the initial force.

13. The chair of claim 6, wherein the initial force corresponds to a seated body weight of the patient, and wherein the first selected portion of the initial force corresponds to about 10% of the initial force (about 90% of the initial force being removed from the seat portion).

14. The chair of claim 13, wherein the second selected portion of the initial force corresponds to about 90% of the initial force.

15. The chair of claim 11, wherein the processor is configured to determine the minimum threshold force and the maximum threshold force based on the seated body weight for each respective patient who uses the chair.

16. A method of administering a standardized performance test to a patient, comprising:
   seating the patient on a chair, the chair comprising:
      a seat portion;
      a base portion;
      a support element extending between the base portion and the seat portion, the support element configured to support the seat portion, wherein a position of the seat portion relative to the base portion is selectively adjustable relative to a vertical axis;
      a force sensor operatively coupled to one of the seat portion, the base portion, and the support element, wherein the force sensor is configured to produce an output signal indicative of the force applied to the force sensor;
      a timer configured to provide an output indicative of a recorded time interval; and
      a processor positioned in operative electrical communication with the force sensor and the timer, the processor being configured to receive the output signal from the force sensor;
   using the processor of the chair to initiate timing of the standardized performance test by the timer in response to receiving an output signal from the force sensor corresponding to a force value less than or equal to a minimum threshold force, wherein the minimum threshold force is indicative of a rising of the patient from the seat portion of the chair;
   using the processor of the chair to cease timing of the standardized performance test by the timer in response to receiving an output signal corresponding to a force greater than or equal to a maximum threshold force, wherein the maximum threshold force is indicative of a reseatinq of the patient on the seat portion of the chair; and using the processor to determine a time interval of the standardized performance test based upon the output of the timer.

17. The method of claim 16, further comprising selectively adjusting a vertical position of the seat portion relative to the base portion.

18. The method of claim 16, further comprising using the processor to transmit the time interval to a display.

19. The method of claim 18, wherein the processor transmits the time interval to the display through an information port.

20. The method of claim 18, wherein the processor transmits the time interval to the display through a wireless connection.

* * * * *